United States Patent [19]
Copeland et al.

[11] Patent Number: 5,840,572
[45] Date of Patent: *Nov. 24, 1998

[54] BIOLUMINESCENT BIOASSAY SYSTEM

[75] Inventors: Hugh D. Copeland, Chula Vista; David Lapota, San Diego; Dena E. Rosenberger, El Cajon; Gary F. Mastny, San Diego, all of Calif.

[73] Assignee: United States of America as represented by the Secretary of the Navy, Washington, D.C.

[*] Notice: The term of this patent shall not extend beyond the expiration date of Pat. No. 5,565,360.

[21] Appl. No.: 688,133

[22] Filed: Jul. 29, 1996

Related U.S. Application Data

[63] Continuation-in-part of Ser. No. 321,066, Oct. 11, 1994, Pat. No. 5,565,360.

[51] Int. Cl.$^6$ .................................................. C12M 3/00
[52] U.S. Cl. ...................................... 435/286.7; 435/288.7; 435/808; 356/427; 422/82.05; 422/82.09
[58] Field of Search ............................... 356/427; 422/52; 435/286.7, 288.7, 808

[56] References Cited

U.S. PATENT DOCUMENTS 5,264,906  11/1993  Ferer et al. .................................. 356/28
5,565,360  10/1996  Lapota et al. ........................ 435/286.7
5,580,785  12/1996  Stiffey et al. ........................ 435/288.7

OTHER PUBLICATIONS

Lapota et al., "The Use of Stimulable Bioluminescence from Marine Dino Flagellates as a Means of Detecting Toxicity in the Marine Environment." Standard Technical Publication 1216, American Society for testing and Materials 1994.

*Primary Examiner*—David A. Redding
*Attorney, Agent, or Firm*—Harvey Fendelman; Peter A. Lipovsky; Michael A. Kagan

[57] ABSTRACT

A system for measuring toxicity levels of a solution includes a water proof sample container transparent to visible light which holds an aqueous test solution containing bioluminescent organisms. A light tight chamber has a cavity which holds the sample container and includes a light port. A stress generating system positioned in the sample container generates pressure pulses which stimulate the organisms to generate light emissions. A light detector system mounted to the light tight chamber in a light tight manner detects light emissions generated in the sample container which propagate through the light port and are received by the light detector system. The light detector system generates an electric pulse in response to detecting each detected light emission. A controller enables the stress generating system and the light detector system, and then counts the electric pulses within a predetermined period of time. The system may further include a fiber optic bundle for propagating light from the light port to the photodetector element in the light detector system, and an optical attenuator supervised by the controller to limit the intensity of light irradiating the photodetector within the linear response range of the element, and to prevent ambient light from saturating and damaging the photodetector.

33 Claims, 15 Drawing Sheets

BIOLUMINESCENT BIOASSAY SYSTEM

CROSS REFERENCE TO RELATED APPLICATION

This is a continuation-in-part of application Ser. No. 08/321,066, filed 11 Oct. 1994 now U.S. Pat. No. 5,565,360.

BACKGROUND OF THE INVENTION

The present invention relates to the field of detecting bioluminescent emissions and, more particularly, to counting photonic emissions of an aqueous solution of bioluminescent organisms to determine toxicity levels of the solution.

Bioluminescence is a visible blue light produced either intermittently or continuously by numerous terrestrial and aquatic organisms. Many marine dinoflagellate species are able to produce bioluminescence as part of their daily physiological processes. Similarly, some marine bacteria are also bioluminescent. Since various toxicants are known to reduce the light intensity output of bioluminescent bacterial cultures, they have been used as test organisms to detect the toxicity of atmospheric samples, herbicides, and some chemicals.

Phytoplankton bioassays are effective biological tools to assess environmental contamination because they are primary producers in the food chain, and their inherent sensitivity to toxic chemicals. Phytoplankton bioassays tend to be simple, rapid, and inexpensive when compared to more complicated and involved assays that use fish or invertebrate species. Phytoplankton bioassays generally involve the enumeration of phytoplankton cells to determine stress in algal populations when exposed to a single toxicant or chemical mixtures. These assays have been successful, but tend to be labor intensive.

U.S. Pat. No. 4,950,594, "Microbiological Assay Using Bioluminescent Organism" describes a method for assaying drilling fluids for toxicity. The method consists of agitating an aqueous solution of bioluminescent organisms, *Pyrocystis lunula*, using a stirring rod fitted into the chuck of a variable speed motor. The rod is stirred at approximately 100 rpm to stimulate the organisms to luminesce. Bioluminescence is measured with a solid state photometer circuit as described in U.S. Pat. No. 4,689,305 which provides an output current proportional to the light detected by an integrated photo detection assembly. Since the '305 circuit operates in a current mode, the integrated photo detection assembly only detects average intensity. The circuit is not sensitive enough to detect individual photons generated by the organisms.

U.S. Pat. No. 4,563,331, "System For Measuring Bioluminescence Flash Kinetics" describes a system for detecting and measuring bioluminescent signatures of planktonic organisms. The system includes a light tight chamber in which is positioned an organism sample holder containing filtered seawater and bioluminescent organisms. Photomultiplier tubes are mounted to the light tight chamber to detect any light generated by the organisms. The organisms are stimulated to luminesce by a vacuum pump which draws the seawater through a filter from the bottom of the sample holder. Signals generated by the photomultiplier tubes in response to detecting the light emissions from the organisms are provided to Davidson multichannel analyzers.

In the operation of the '331 system, the vacuum pump draws seawater through the filter at the bottom of the sample holder. The suction causes the organism to be drawn against the inlet side of the filter, where they concentrate. This tends to damage the organisms. Moreover, light generated by organisms squeezed between other organisms is not detected by the photomultiplier tubes, and further, the amount of light they produce can be highly variable. Variations in time delays between energizing the vacuum pump and initiating data collection between experiments as a result of manual operation of the '331 system introduces a variable in the experimental results. This variable makes it difficult to relate the results of one experiment to another, negatively impacting the repeatability of experiments performed using the '331 system.

Therefore, there is a need for a bioluminescent assay system in which the bioluminescent organisms may be stimulated without being damaged, and in which the stimulus is consistent. A further need exists for a bioluminescent system which provides good repeatability between experiments.

DESCRIPTION OF THE DRAWINGS

Throughout the several views, like elements are referenced with like references.

SUMMARY OF THE INVENTION

A system for measuring toxicity levels of a solution includes a water proof sample container transparent to visible light which holds an aqueous test solution containing bioluminescent organisms. A light tight chamber has a cavity which holds the sample container and includes a light port. A stress generating system positioned in the sample container generates pressure pulses which stimulate the organisms to generate light emissions. A light detector system mounted to the light tight chamber in a light tight manner detects light emissions generated in the sample container which propagate through the light port and are received by the light detector system. The light detector system generates an electric pulse in response to detecting each detected light emission. A controller enables the stress generating system and the light detector system, and then counts the electric pulses within a predetermined period of time.

The invention may include a fiber optic bundle for propagating the photonic emissions of the bioluminescent organisms from the light port to the photodetector in the light detector system. The light detector system may further include an optical attenuator supervised by the controller to limit the intensity of light irradiating the photodetector element within the linear response range of the photodetector, and to prevent ambient light from saturating and damaging the photodetector.

In another aspect of the invention, the stress generating system may be implemented as an acoustic transducer upon which the sample container rests, thereby eliminating direct contact between the stress generating system and the test solution.

An important advantage of the present invention is that it provides an automatic system for determining relative toxicity levels in aqueous solutions.

A further advantage is that the present invention provides good test result repeatability with low statistical variance.

Another advantage of the present invention is that it includes a hardware based safety interlock system which prevents the optical detector system from being damaged from exposure to ambient light.

Yet another advantage of the invention is that it incorporates a bar code scanning system to keep track of test sample solutions.

A still further advantage of the invention is that it includes an optical attenuator for preventing ambient light from accidently saturating, and hence damaging the photodetector, and for limiting the intensity of light irradiating the photodetector within the linear response range of the photodetector.

Another advantage of the invention is that includes a vibration generating system for generating pressure pulses in the test solutions that does not require direct contact with the test solution.

These and other advantages will become more apparent upon review of the specification and drawings herein.

DESCRIPTION OF THE PREFERRED EMBODIMENT

First Embodiment

Figure 1:
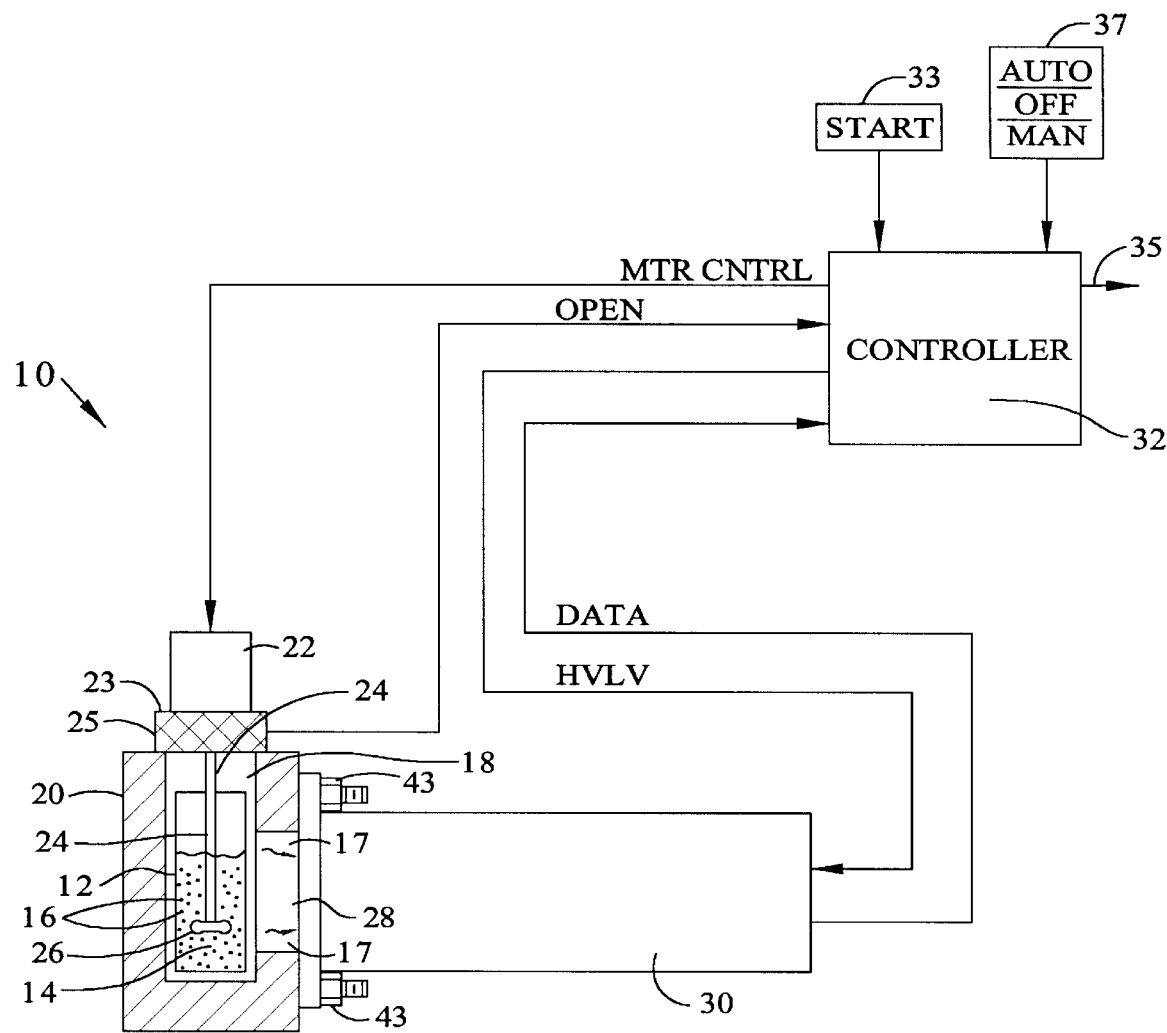
FIG. 1 is a diagram of a bioluminescent bioassay system embodying various features of the present invention.

Referring now to FIG. 1, there is shown a partial cross-sectional view of a bioluminescent assay system 10 for measuring toxicity levels in an aqueous solution containing light emitting organisms. System 10 is shown to include an optically transparent sample container 12 for holding a test sample of an aqueous solution 14 of bioluminescent organisms 16 which is to be tested for toxicity. The bioluminescent organisms 16 are selected so as to generate photonic emissions 17, or light when subjected to pressure pulses, such as turbulence, in the aqueous solution 14. The sample container 12 is mounted within a cavity 18 formed in a light tight chamber 20. Stress generating means for stimulating the organisms 16 to generate photonic emissions (light) 17 may include a motor 22 having a motor output shaft 24 on which a propeller 26, or other stirring type of mechanism, such as a paddle, is mounted. The motor 22 is mounted to the top of a cap 25 which fits over the light tight chamber. The shaft 24 extends into the sample container 12 so that the propeller is immersed in the aqueous solution 14. Energizing the motor 22 causes the propeller 26 to stir the aqueous solution 14, thereby generating shear stresses, or pressure pulses in the fluid 14 which tend to simulate the organisms 16 to emit light. The motor 22 is mounted on top 23 of a cap 25 fitted to the upper end of the chamber 20 so as to create a light tight seal so that ambient light does not enter the chamber 20. The chamber 20 includes a light port 28 through which photonic emissions 17 generated by the organisms propagate through light port 28 to an optical detector system 30 mounted in a light tight manner on the chamber 20 which detects any photonic emissions 17 generated by the organisms 16. The optical detector system 30 is mounted to the chamber 20 in a manner which prevents ambient light from entering the chamber 20 or reaching the light sensing element 164 (FIG. 7) of the optical detector system 30. A controller 32 enables the optical detector system 30 and the stress generating system for stimulating the organisms 16. In the preferred embodiment, the controller 32 may be implemented as an imbedded micro-controller. A sensing circuit, not shown, partially located in the cap 25 provides an output signal OPEN to the controller 32 which represents whether the cap 25 is properly positioned on top of the chamber 20 so as to prevent ambient light from reaching the optical detecting system 30. Should the cap 25 be positioned so that ambient light enters the chamber 20, the signal OPEN is a logic low, causing the controller 32 to disable power to the photo detection circuit 30.

The system 10 also includes a start switch 33 coupled to the controller 32 which allows the optical detector system 30 and motor 22 to be automatically enabled in an appropriate time sequence. A second switch 37 operably coupled to the controller 32 and to the optical detector system 30 in accordance with well known techniques provides a human operator with the option of operating the system 10 in an automatic or manual mode, or of disabling the system altogether when the switch 37 is placed in the OFF position. Positioning the switch 37 in the automatic mode enables the motor 22 through the motor control (MTR CNTRL) line, and enables the optical detector system 30 by way of the "high-voltage-low-voltage" (HVLV) signal line. The optical detector system 30 generates an electronic signal pulse in response to receiving each single photonic emission 17. Each signal pulse is provided to the controller 32 via the DATA signal line. When operated in an automated mode, the controller 32 counts the number of signal pulses generated by the optical detector system 30 within a predetermined period of time.

The sample container 12, may for example, be a cuvette made of a material such as polystyrene which is optically transparent to the wavelengths of photonic emissions of interest generated by the bioluminescent organisms 16. Such wavelengths generally fall within the range of about 450–500 nanometers.

Figure 2:
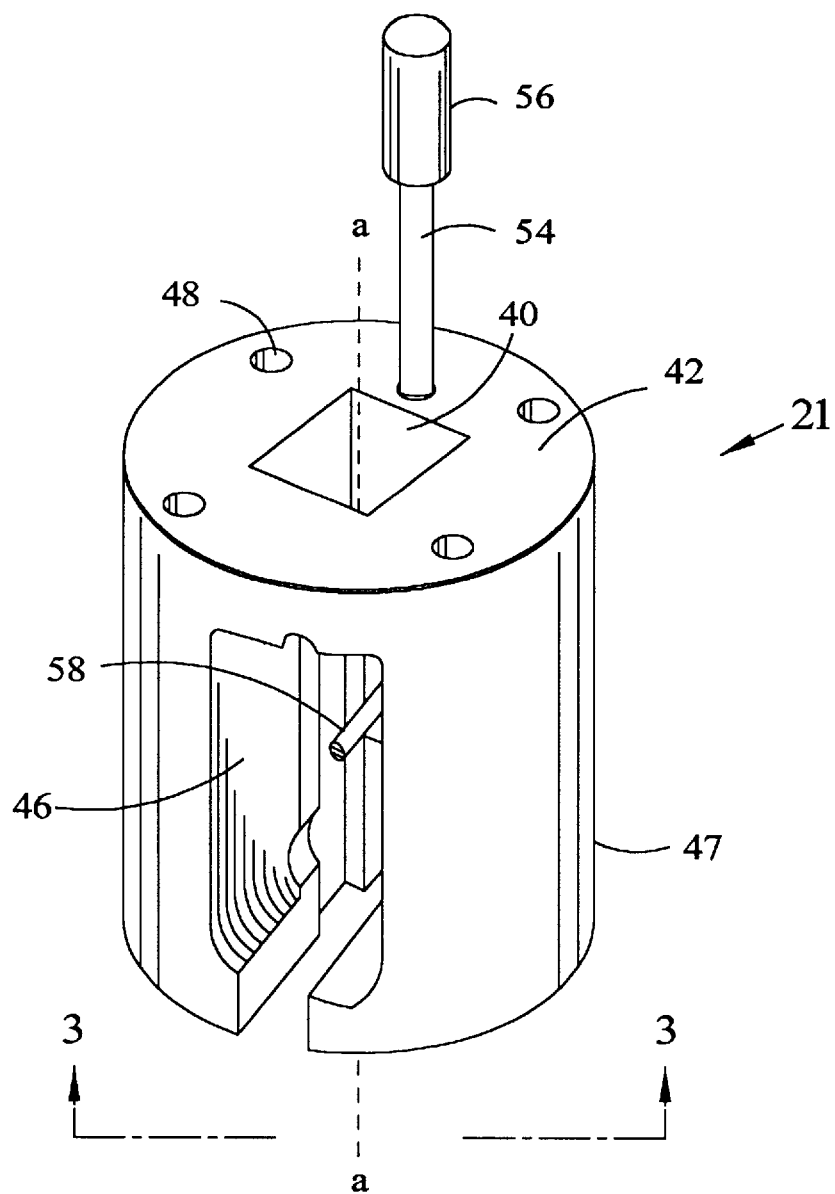
FIG. 2 is a perspective view of the sample support.
Figure 3:
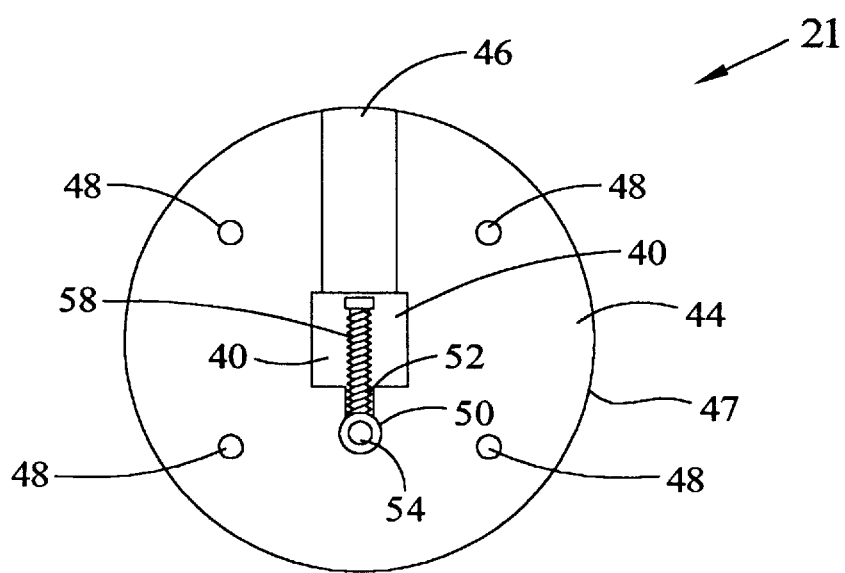
FIG. 3 is an end view of the sample support taken along section 3—3 of FIG. 2.

In the presently preferred embodiment, as shown in FIG. 2, a sample support 21 is used to support the sample container 12 within the light tight chamber 20. The sample support 21 may be generally cylindrically shaped, as shown in FIGS. 2 and 3. Sample support 21 may include a cavity 40 extending from a first planar surface 42 through to the opposite planar surface 44 (FIG. 3) generally along the direction of the longitudinal axis a—a of the sample support 21. The support 21 further includes a light port 46 extending radially outwardly from the cavity 40 through to the surface 47 of the sample support 21. By way of example, the cavity 40 preferably may have a cross-sectional area shaped, by way of example, as a square, which allows the sample container 12 to slide and be supported within the cavity 40 without rotation. However, it is to be understood that the cavity 40 may have a cross-sectional area configured into other shapes, such as circles, triangles, or rectangles. Mounting holes 48 which extend the longitudinal length between the opposed planar surfaces 42 and 44 generally parallel to the axis a—a receive threaded fasteners, not shown, for fastening and indexing the sample support 21 to the chamber 20.

As more clearly seen in FIG. 3, a generally round slot 50 having a keyway 52 extends generally from the surface 42 to the surface 44 down along the longitudinal length of the sample support 21 and parallel to the axis a—a so as to be in fluid communication with the cavity 40. Referring also to FIG. 2, a rod 54 having a handle 56 is fitted to slide within the generally circular slot 50. A strut 58 extending generally perpendicular from the rod 54 and through the keyway 52 towards the cavity 40 towards its bottom allows the rod to slide and be retained within the slot 50 by the surface 42 because the keyway 52 extends only from the bottom surface 44 to within a fixed, discrete distance, as for example 0.5 inches, from below the surface 42. Thus, the strut 58 retains the rod within the slot 50. The combination of the rod 54 and strut 58 provides a lift mechanism for facilitating removal of the sample container 12 from the cavity 40 by pulling on the handle 56, causing the strut 58 to lift the bottom of the sample container 12 up out of the cavity 40.

Figure 7:
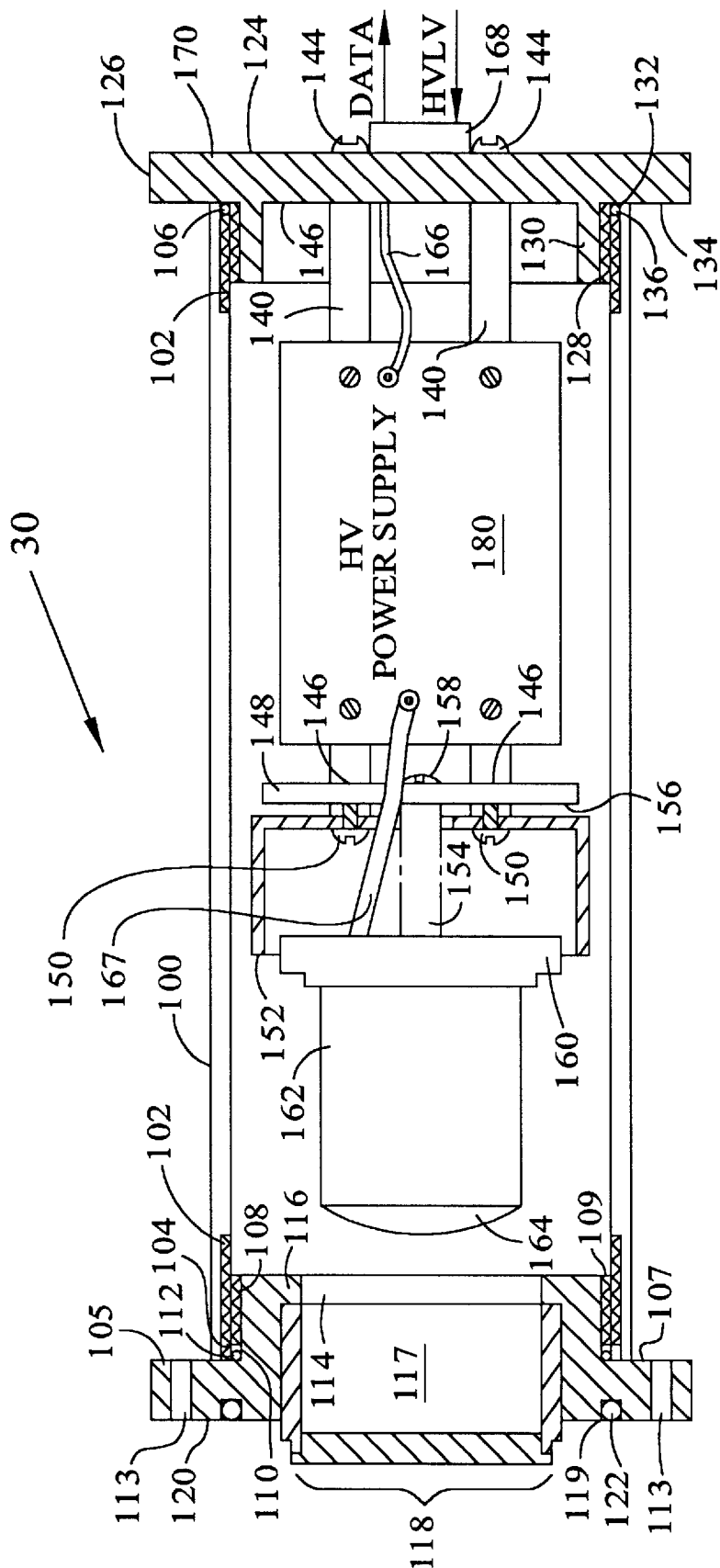
FIG. 7 is a cross-sectional view of the optical detector system.

The light tight chamber 20, described with reference to FIG. 4, includes a cavity 60 extending along the longitudinal axis b—b between opposed planar surfaces 61 and 53. At the top of the chamber 20, the cavity 60 is defined by an annulus 55 extending up from the planar surface 62. The annulus 55 includes a groove 57 in which an O-ring 65 is placed. The cavity 60 is shaped to slidably receive the sample support 21 so that the aperture 46 of the sample support 21 may be aligned with a circular aperture 64 generally centered about an axis c—c which preferably is perpendicular to and intersects the longitudinal axis b—b. The aligned apertures 46 and 64 of the sample support 21 and light tight chamber 20, respectively, collectively comprise the light port 28. The aperture 64 preferably is sized to receive an optically neutral density filter 118 (FIG. 7). The use of the filter 118 extends the dynamic counting range of the system. An annular planar surface 66 formed in the chamber 20 and centered about the aperture 64 provides a mounting surface so that the optical detector system 30 may be attached to the chamber 20 in a light tight manner. Three threaded studs 68 extending perpendicularly from the surface 66 are used to fasten the optical detector system 30 to the chamber 20 as shown in FIG. 1.

Figure 4:
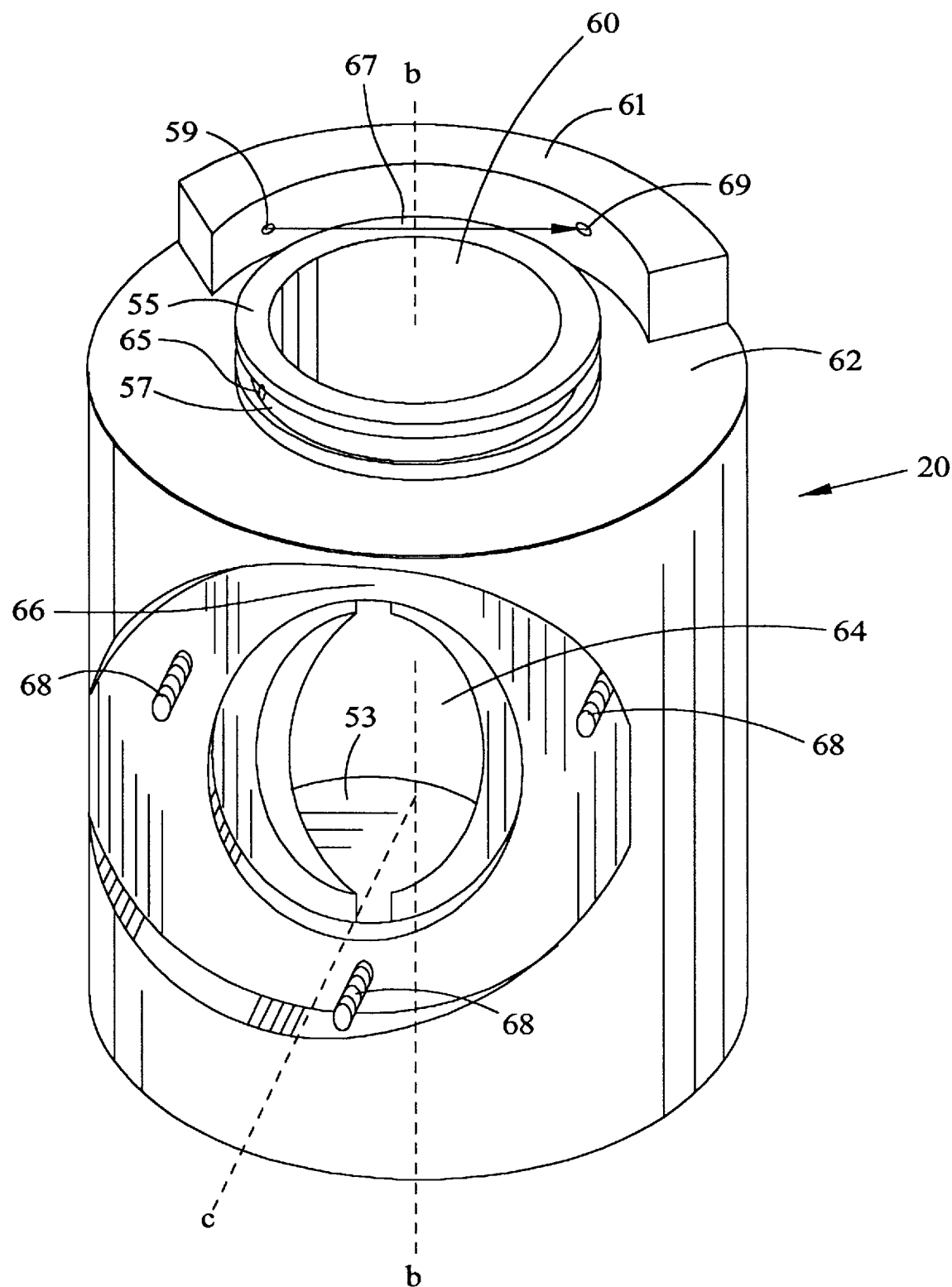
FIG. 4 is a perspective view of the light tight chamber.
Figure 5:
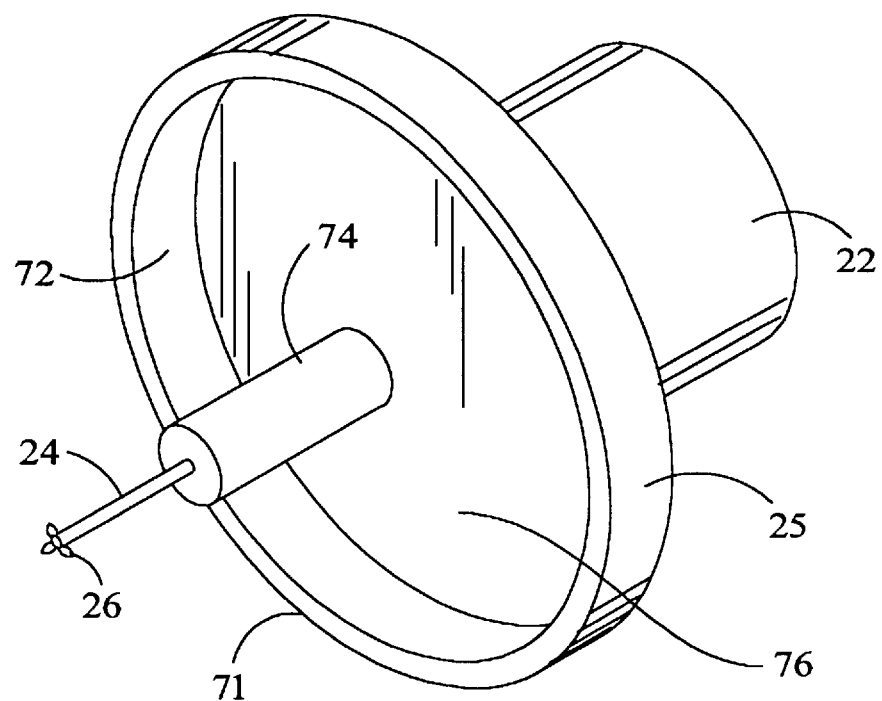
FIG. 5 is a three-quarter view of the cap and motor assembly.
Figure 6:
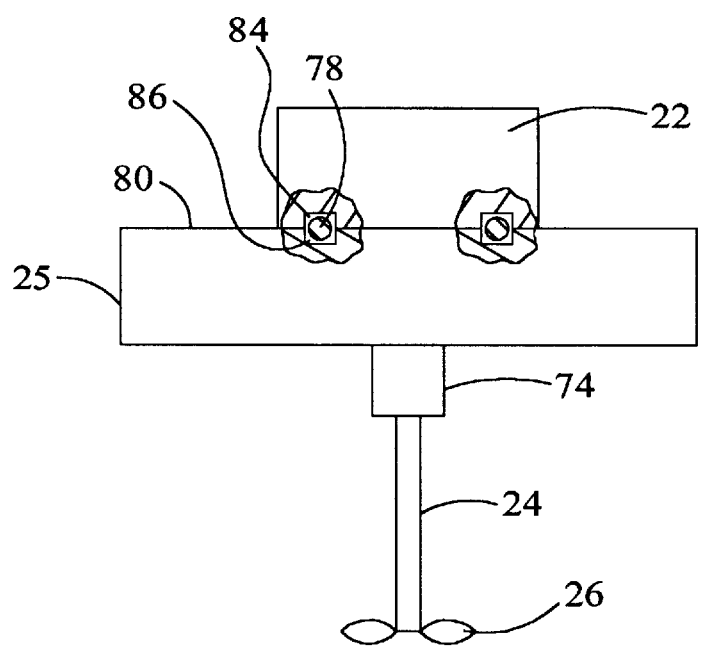
FIG. 6 is a partial cross-sectional view of the cap and motor assembly.

By way of example, with reference to FIGS. 4, 5 and 6, collectively, the motor 22 is rigidly mounted to a cap 25 having an annulus 71 with an internal diametral surface 72 sized to fit over the O-ring 65 supported in the groove 57 of the annulus 55 on top of the container 20. A slight interference fit between the internal diametral surface 72 and the O-ring 65 assures a light tight fit between the cap 25 and the chamber 20. The motor shaft 24 extends through an aperture, not shown, in the cap 25, and is supported by an annulus 74 extending from the inner planar surface 76 of the cap. In order to assure that no ambient light penetrates between the motor and the cap 25, by way of example, a resilient sealing member 78, such as a gasket or O-ring, may be fitted between the motor 22 and the surface 80 of the cap 25. The sealing member 78 is preferably fitted between an annular groove 84 formed in the housing of the motor 22 and an annular groove 86 formed in the surface 80 of the cap 25. The end cap 25, light tight body 10, and sample support 21 are preferably made of a material which is chemically nonreactive with sea water, as for example, DELRIN®, polycarbonate, or polystyrene.

An example of one preferred optical detection system 30 is described with reference to FIG. 7, where there is shown a cylinder 100 having internal threads 102 at ends 104 and 106. An end ring 107 having a flange 105 and an inner annulus 109 with external threads 108 is threaded into the internal threads 102. An annular land 110 on the inner annulus 109 provides a surface for receiving an O-ring 112. When the end ring 107 is threaded into the cylinder 100, the O-ring 112 is compressed between the flange 105 and the cylinder end 104 to provide a light tight seal. The end ring 107 also includes an inner aperture 114 and a coterminous outer aperture 117 which define an inner flange 116 at their interface. The outer aperture 117 is sized to slidably receive an optional filter 118 with minimal clearance. The flange 116 provides a backstop for the filter 118. By way of example, the filter 118 may be implemented as any of an Oriel Model Nos. 59980, 59990, or 59000. The outer planar surface 120 of the flange 105 has an annular groove 119 for receiving an O-ring 122 which is compressed to provide a light tight seal when the optical detection system is attached to the light tight body 20. Apertures 113 extending through the flange 105 around its outer periphery slide over the studs 68 (FIG. 4) to facilitate mounting and attaching the optical detection system 30 to the light tight chamber 20 with nuts 43 as shown in FIG. 1.

Still referring to FIG. 7, the optical detection system 30 further includes an end cap 124 having an outer flange 126 and external threads 128 formed in an annulus 130. An annular land 132 between the external threads 128 and the inner planar surface 134 of the flange 126 supports an O-ring 132 which is compressed to provide a light tight seal between the end cap 124 and the cylinder 100. A pair of struts 140 extend perpendicularly from the inner surface 146 of the end cap 124. The struts 140 may be attached to the end cap 124 using threaded fasteners 144 which extend through the end cap and into the struts 140. The ends 146 of the struts 140 support a disc shaped mounting plate 148 which is attached to the struts by threaded fasteners 150. The threaded fasteners 150 also attach an electrically insulating, concentric ring spacer 152 to the end plate 148. The outside diameter of the spacer 152 preferably is slightly less than the inside diameter of the cylinder 100 so that the spacer may minimize any wobbling of the struts 140 and the mounting plate 148 within the cylinder 100. A pair of struts 154 (only one is shown) extend perpendicularly from the surface 156 of the support plate 148 from which they are attached with threaded fasteners 158 (only one is shown). The struts 154 support a socket 160 in which is mounted a photomultiplier tube 162 having a light sensing element 164, or lens, which receives the photonic emissions 17 generated by the organisms 16. Also supported by the struts 140 is a high voltage (HV) power supply 180 which provides power to the photomultiplier tube 162. The HV power supply 180 may be implemented, for example, as a Venus Scientific, Inc., Model C30. Electrical coupling link 167 provides a power and data link between the photomultiplier tube 162 and the HV power supply 180. Electrical coupling link 167 provides a power and data link between the HV power supply 180 and electrical socket 168 mounted on the external planar surface 170 of the end cap 124. The photomultiplier tube 162 may be implemented as an RCA, Model 8575 photomultiplier tube ("PMT") operated in the single photon counting mode. The cylinder 100, end ring 107, and end cap 124 are preferably made of a ferrous material to provide a magnetic shield which prevents external magnetic fields from influencing the propagation of photoelectrons in the photomultiplier tube 162. Such ferrous material should be chemically nonreactive with sea water, and may be for example, stainless steel or μ-metal.

Figure 8:
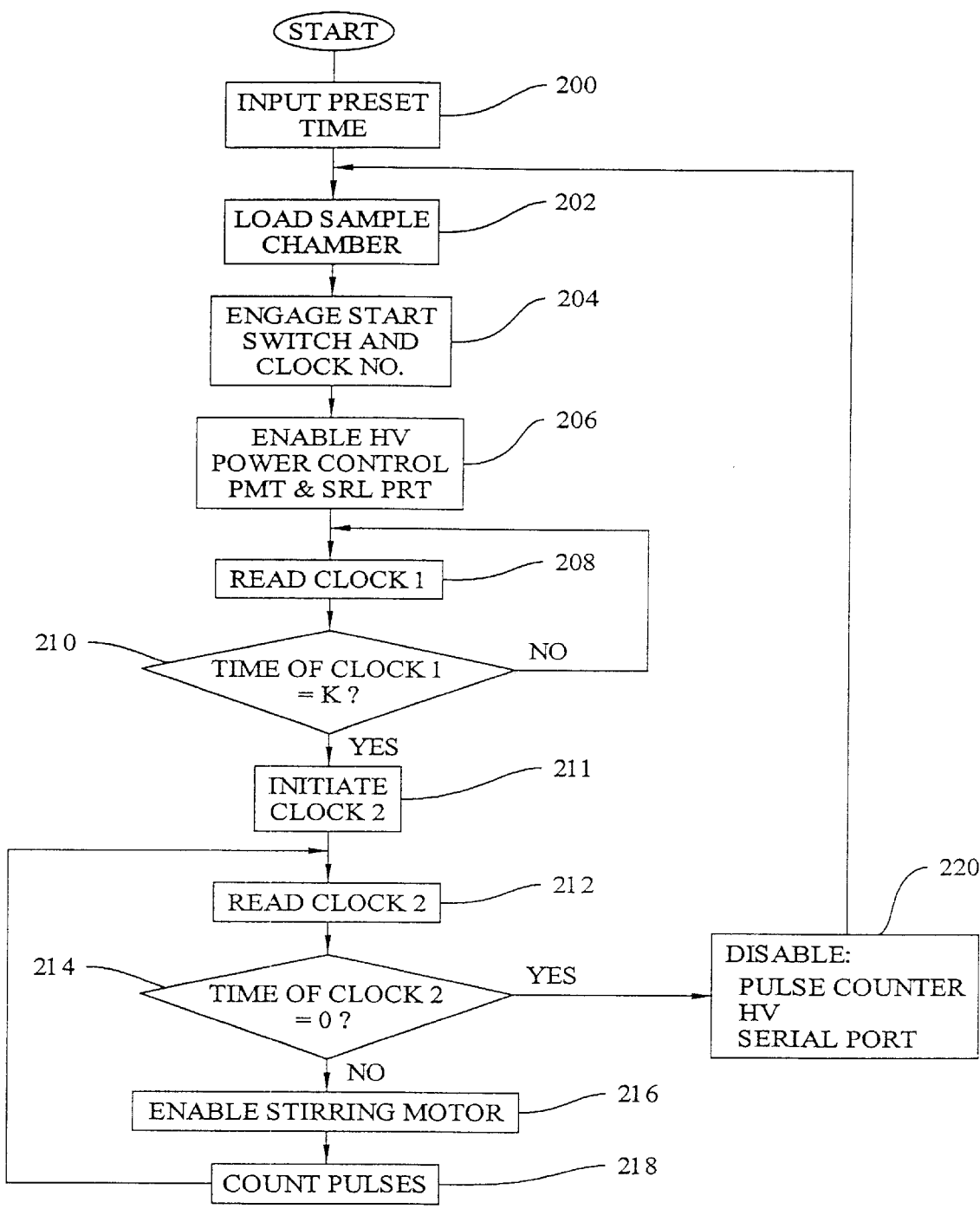
FIG. 8 is a flow chart of the operation of the invention.

The operation of the system 10 is described with reference to FIG. 8. The system 10 is initialized by providing an input representing the desired counting time, "TIME", to the controller 32 at step 200. The counting time refers to the period in which electronic pulses corresponding to the photonic emissions 17 generated by the bioluminescent organisms 16 are to be counted. Next, at step 202, the aqueous sample solution 14 with the bioluminescent organisms 16 may be placed in the sample holder 12. The sample holder 12 is placed in the sample support 21 which is mounted within the light tight chamber 20. A human operator then mounts the cap 25 on the light tight body 20. At step 204, the operation of the controller 32 is initiated by pushing the "START" switch 33 which enables the HV power supply 180 and photomultiplier tube 162 and initiates a first internal clock, CLOCK 1, in the controller 32. A predetermined period, for example, of five seconds elapses in order to stabilize the HV power supply 180. The controller 32 proceeds to enable the HV power supply 180 and photomultiplier tube 162, as well as the serial port at step 206.

The controller 32 then reads the first clock at step 208. A decision is made by the controller at step 210 to determine if the time elapsed from the initiation of the first clock equals a predetermined value, K. If the determination at step 210 is "NO", then the controller 32 returns to step 208. If the determination at step 210 is YES, the controller 32 initiates a second clock, CLOCK 2, at step 211 which counts down from a time, d+TIME, where "d" represents a delay, by way of example, of two seconds to assure that the organisms 16 have not been pre-stimulated. Pre-simulation would tend to invalidate the total pulse count. In general, the time delay provides a "dark count" which is actually insignificant compared to the photon count generated by stimulated organisms (approximately 400 counts out of typically 300,000 to 1,000,000 counts). The dark count refers to the number of photons generated by thermionic emissions from the photocathode and dynode chain in the photomultiplier tube 162 and to light generated by the organisms 16 when they are not being stimulated. The controller then reads CLOCK 2 at step 212. Proceeding to step 214, the controller 32 determines if the time indicated by the second clock equals zero. If the determination at step 214 is "NO", the controller 32 enables the stirring motor 22 at step 216, and then at step 218, allows the controller to count pulses generated by the optical detecting system 30. The controller 32 then returns to step 212. If the determination by the controller at step 214 is "YES", then at step 220, the controller 32 disables the HV power supply 180, stirring motor 22, and serial port 35, and ceases to count pulses generated by the optical detecting system 30. The operation of the system then returns to step 202.

While CLOCK 2 decrements, any photons emitted by the organisms 16 detected by the optical detector system 30 cause the photomultiplier 162 to generate an electric pulse which is counted by the controller. Generally, while CLOCK 2 is decrements, output data including elapsed time and count data are sent to output port 35, such as an RS-232 serial port, of the controller 32. Thus, the data may be sent to a remote computer to log and analyze data, or to a peripheral device such as a printer.

Figure 9:
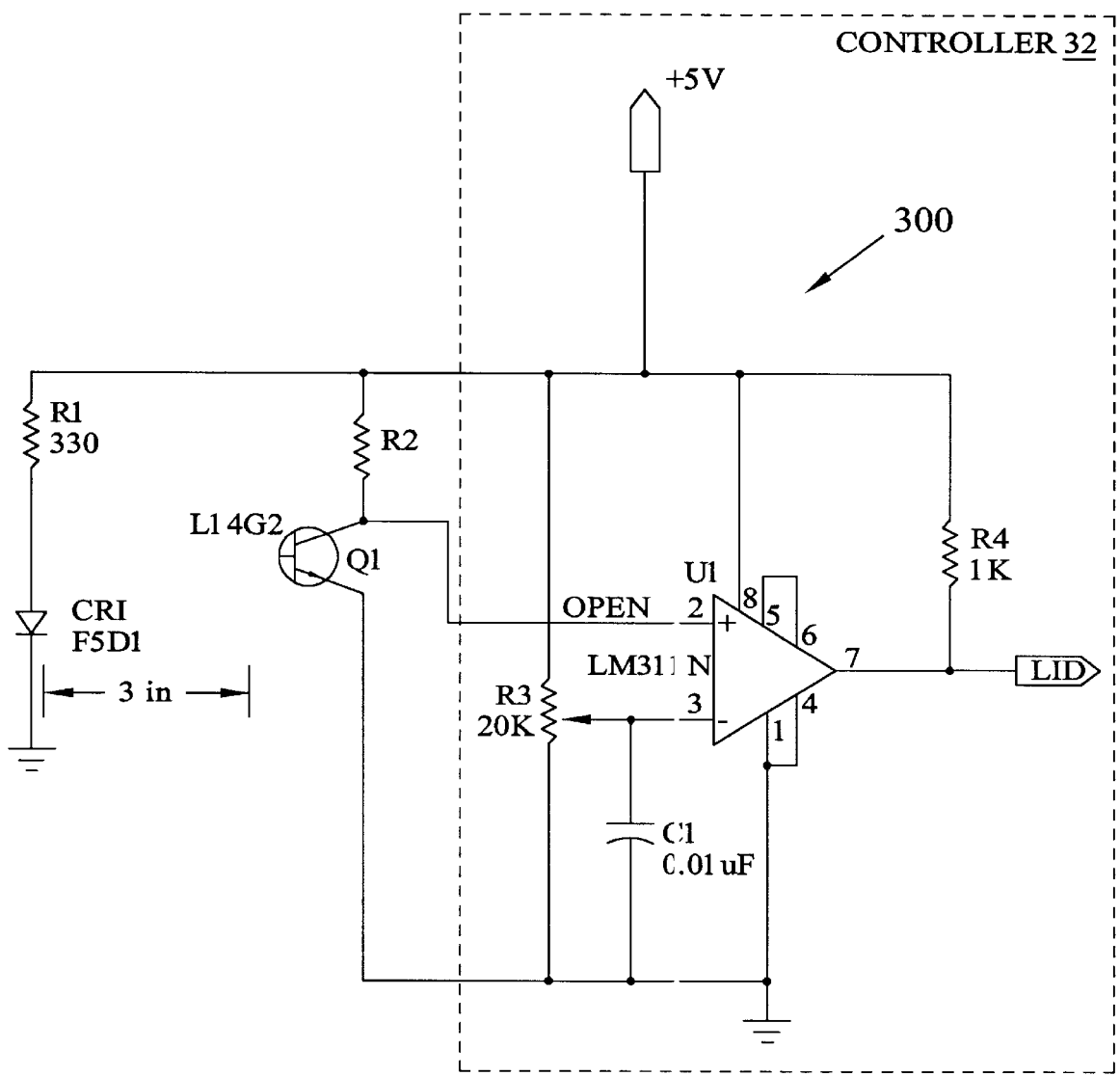
FIG. 9 is a schematic diagram of a light detector circuit.

Referring to FIG. 9, the system 10 also includes a light detector circuit 300, included within the controller 32, which causes the optical detector system 30, and particularly, the photomultiplier 162, to be disabled in the event that the cap 25 is removed from the light tight body 20 in order to prevent damaging the photomultiplier 162 from optical overload. Once the light detector circuit 300 causes power to the HV power supply 180 to be turned off, the photomultiplier 162 is disabled. Power to the HV power supply 180 is not restored until switch 37 (FIG. 1) is toggled switched to its "OFF" position and then back to either its manual or automatic select position, thereby providing the system 10 with a safety interlock.

Referring now to FIG. 9, there is shown an example of light detector circuit 300 which includes an infrared energy emitting diode CR1 which is mounted in an arcuate shaped block 61 (FIG. 4) so that it irradiates infrared energy through the aperture 59 along a path 63 which is occluded by cap 25 when the cap is mounted over annulus 67, but which irradiates the phototransistor Q1 which receives the infrared energy through aperture 69 when the cap 25 is dislodged or removed from the annulus on top of the light tight body 20. By way of example, the distance between CR1 and Q1 may be about three inches.

When the cap 25 (FIGS. 5 and 6) is positioned on the annulus 55 (FIG. 4) so that ambient light does not enter the light tight body 20, the gate voltage of phototransistor Q1 is sufficiently low so that there is very low conduction from the +5V supply through resistor R2 down to ground. When the gate voltage of Q1 is low, the input signal, OPEN, at pin 2 of comparator LM311N is high, whereupon the output, LID, of the comparator is a logic high. In other words, when the infrared light path between diode CR1 and phototransistor Q1 is blocked, or occluded, i.e., no ambient light enters the light tight chamber 20, the output of the comparator LM311N is a logic high. However, when infrared energy generated by the diode CR1 is detected by the phototransistor Q1, the gate voltage is sufficient so that the 5V source conducts through the phototransistor Q1 to ground. In such case, the input 2 of LM311N is relatively low, whereupon the output, LID, of the comparator LM311N is a logic low. Thus, it may be appreciated that the light detecting circuit 300 provides an output LID which represents whether ambient light is or is not entering the light tight chamber 20. Output LID is provided to a high voltage interlock circuit 182 (FIG. 10) which allows the photomultiplier tube 162 to be energized only at appropriate times, and to prevent damage to the photomultiplier tube 164. Damage could occur, for example, when the cap 25 is removed from the light tight body 20, whereupon the photomultiplier tube 164 would, be saturated and overwhelmed by excessive light. The high voltage interlock circuit 182 is part of the controller 32.

Figure 10:
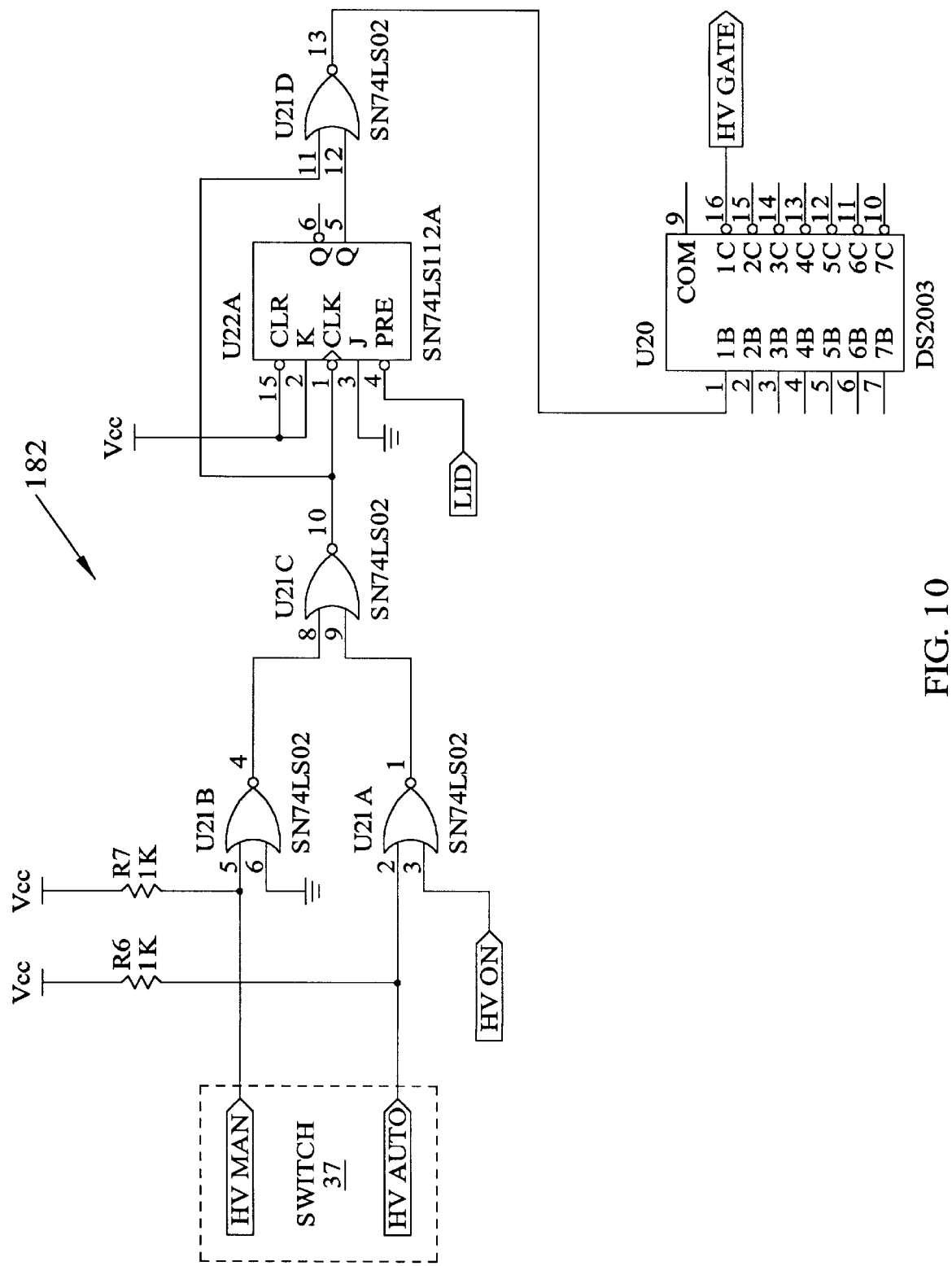
FIG. 10 is a schematic diagram the high voltage power control circuit.

FIG. 10 illustrates an example of a high voltage (HV) interlock circuit ("HV circuit") 182 which performs a safety interlock function that prevents the photomultiplier tube 162 from being energized until the switch 37 (FIG. 1) has been toggled through an OFF position. By way of example, the HV interlock circuit 182 is shown to include four interconnected NOR gates U21A, U21B, U21C, and U21D; a flipflop U22A; and an inverting buffer U20. Flipflop U21B receives a normally logic high HVMAN input at pin 5 and a grounded input at pin 6. Flipflop U21A receives a normally logic high HVAUTO input at pin 2 and a normally logic high HV ON signal input at pin 3. The inputs HVMAN and HVAUTO are connected to the switch 37 so that they are mutually exclusive. The signal input HV ON is provided by the controller 32. In the preferred embodiment of the present invention, the switch 37 also has an OFF position and may be, by way of example, a C&K Model 7103. When switch 37 is in the OFF position, HVMAN and HVAUTO are both at a logic high. The condition where HVMAN is a logic low represents selection by a human operator to operate the system 10 under direct human supervision in a manual mode by positioning the switch 37 in the MAN position. The condition where HVAUTO is a logic low represents selection by a human operator to operate the system 10 under supervision of the controller 32 by positioning the switch 37 in the AUTO position.

The operation of the HV interlock circuit 182 is described with reference to FIG. 10. Assume the case where: 1) a human operator selects switch 37 so as to operate the system 10 in the automatic mode so that HVMAN is a logic high and HVAUTO is a logic low; and 2) that the LID output of the light detector circuit 300 is a logic high, representing that no ambient light penetrates into the light tight body 20. As described with reference to step 206 (FIG. 8), the controller 32 enables the HV power supply 180 and photomultiplier 162, as well as the serial port 35. A logic high provided to the PRESET input of the flipflop U22A allows the positive to negative transition at pin 1 of the flipflop to cause the Q output to go low. In such case, the logic level at pin 12 of NOR gate U21D is also low. Given that the inputs to pins 5 and 6 are high and low, respectively, the output of NOR gate U21B is a logic low. Since the inputs at pins 2 and 3 are both low, the output of NOR gate U21A is a logic high. The input to pins 8 and 9 then are a logic low and high, respectfully, resulting in a logic low output which is provided to pin 11 of NOR gate U21D and to the clock input of the flipflop U22A. The inputs on pins 11 and 12 of NOR gate U21D are then both low. Therefore, the output of NOR gate U21D is a logic high which is fed to inverting buffer U20, thereby generating a complementary HV GATE output which is used to enable the photomultiplier tube 162.

If the output of the light detecting circuit 300 becomes a logic low, indicating ambient light entering the light tight chamber 20, the low logic level provided to the PRESET input of the flipflop U22A, causes the output signal "Q" to be high. Thus, pin 12 of NOR gate U21D is high while the input at pin 11 of NOR gate U21D remains a logic low. This latter condition causes the outputs of NOR gate U21D, and hence the complement of HV GATE to be low. When the complement of HV gate is low, the photomultiplier tube 162 is disabled. Should the LID output provided to the flipflop U22A change from a low state back to a high state, the inputs at pins 11 and 12 of NOR gate U21D will both remain at their present logic state even though pin 11 sees a logic low and pin 12 sees a logic high. Therefore, the output of NOR gate U21D will remain a logic low so that the photomultiplier tube 162 remains disabled. In order to enable the photomultiplier tube 162, the HVAUTO signal must change from a logic low to a logic high, and back to a logic low again whereupon the output of NOR gate U21A changes from logic high to a logic low. The change in the logic level at the output of NOR gate U21C (pin 10) may change from a logic low to a logic high and then back to a logic low by toggling switch 37 through the OFF position so that the CLK input of flipflop U22A sees the falling edge of the changing logic level at pin 10. When the CLK input of the flipflop U22A sees the falling edge of the logic signal at pin 1 of the flipflop, and if the input to the PRESET of the flipflop is a logic high, the output Q becomes a logic low. Now, the logic states of both pins 11 and 112 are low so that the output of NOR gate U21D is a logic high, thereby causing the complementary HV GATE signal to enable the photomultiplier tube 162. Thus, it may be appreciated that the HV interlock circuit 182 provides the important safety function whereby the detection of light by the light detecting circuit 300 causes the photomultiplier tube 162 to become disabled and remain so until after the switch 37 is toggled manually, as described above.

A suitable bioluminescent species which may be used in sample solutions in conjunction with the present invention is *Gonyalaux polyedra* because it is easy to culture, hardy, and has a light output which is sensitive to a variety of toxicants. This species may be maintained in enriched seawater medium (ESM) according to American Society for Testing and Materials Standard Guide for Conducting Static 96-h Toxicity Tests with Microalgae (ASTM 1990). Tetrasodium ethylenediaminetetraacetic acid (EDTA), a chelator, may be removed from preparation of the ESM during assays. Cultures were maintained in 250-mL glass flasks under a light regime of 12:12 (light:dark) at approximately 4000 LUX from cool white bulbs. *Gonyalaux polyedra* was maintained at 18° C. in a controlled temperature bath. Typically, *Gonyalaux polyedra* was cultured at 6 to $8 \times 10^3$ cells/mL.

Second Embodiment

Figure 11:
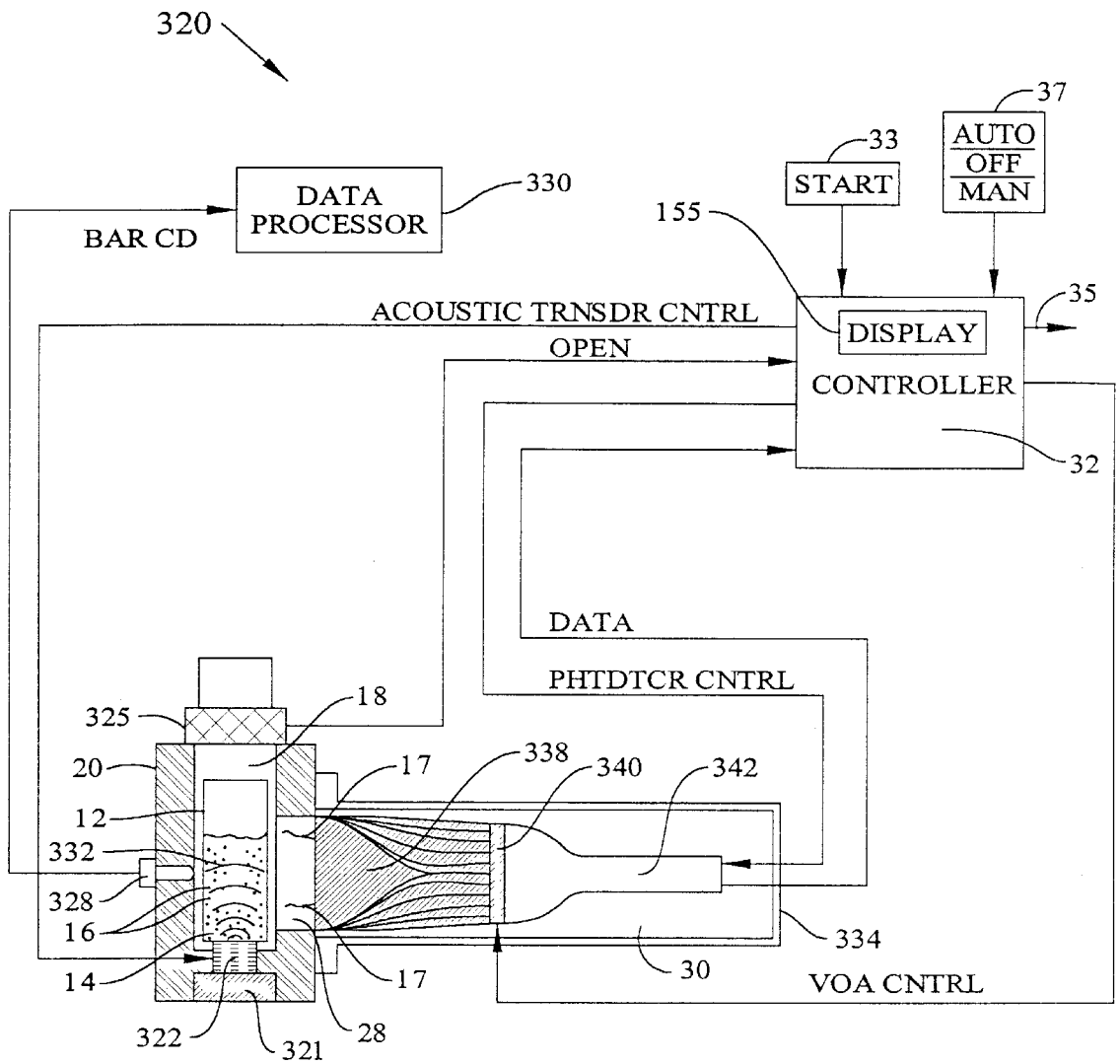
FIG. 11 is a block diagram of a second embodiment of a bioluminescent bioassay system of the present invention.
Figure 12:
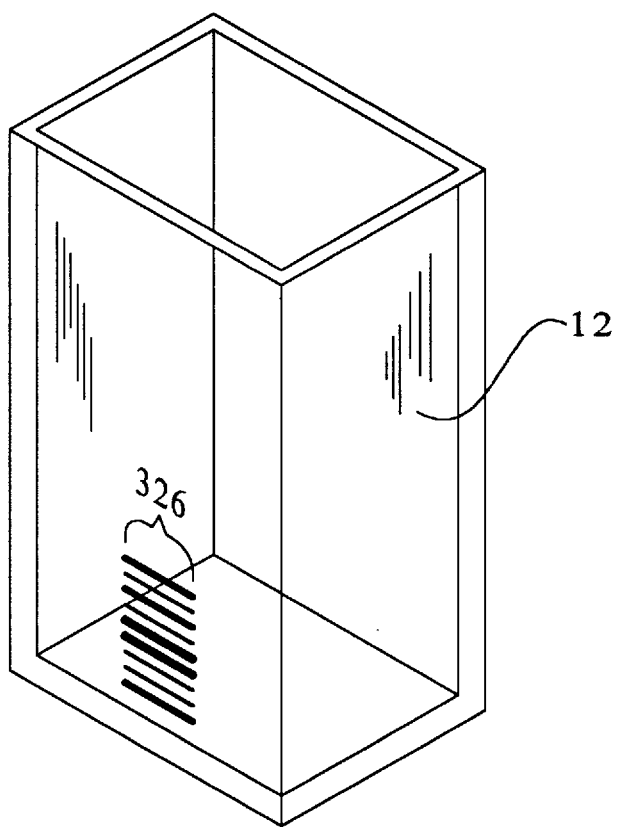
FIG. 12 shows the sample container having a bar code.
Figure 15:
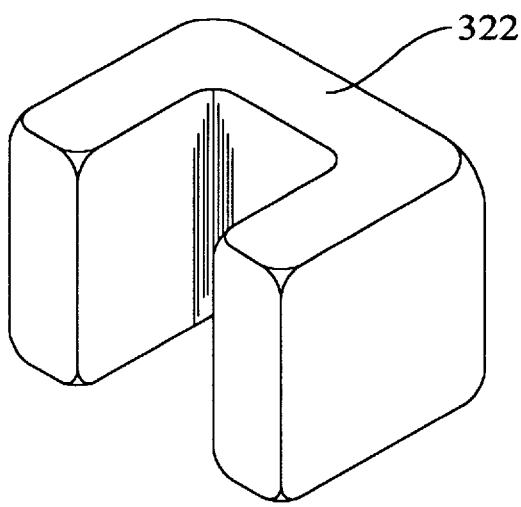
FIG. 15 shows a U-shaped vibrating transducer.

Referring now to FIG. 11, there is shown another embodiment of a bioluminescent assay system 320 of the present invention for testing an aqueous test solution 14 for toxicity by determining the effect of the test solution on the bioluminescent output of bioluminescent organisms 16 placed in the sample. The bioluminescent organisms 16 are selected to generate photonic emissions 17, or light when subjected to pressure pulses 332 in the aqueous solution 14 generated by an acoustic transducer 322 upon which the sample container 12 rests. The sample container 12 is supported within a cavity 18 formed in a light tight chamber 20 which may be of the type described above with reference to FIGS. 1–4. The sample container 12, preferably implemented as a cuvette, rests on a vibration generating system comprising a vibrating transducer 322 affixed to the top of a reaction mass 321. The vibrating transducer 322 may be a U-shaped ultrasonic acoustic transducer or piezoelectric device, as shown in FIG. 15. The purpose of the U-shape for the transducer 322 is to provide a structure having clearance for the strut 58 at the lift end of the rod 54 described with reference to FIG. 2, above. The sample container 12 and cavity 18 may have conforming rectangular cross-sections to specifically orient the cuvette in the light tight chamber within the cavity to facilitate the scanning of bar codes 326 placed on one or more sides of the sample container 12, as shown in FIG. 12. More preferably, the sample container 12 and cavity each may have non-square, rectangular cross-sections. The bar codes 326 are read by a bar code scanner 328 which provides a corresponding bar code signal, BAR CD, to a data processor 330 which stores the bar codes. The bar code scanner 328 and data processor 330 collectively comprise a bar code scanning system. Bar coding the sample chambers 12 is desirable so that the toxicity results may be correlated to a particular test sample 14 by a data processor 330. The reaction mass 321 is mounted to the bottom of the chamber 320 so that the maximum amount of displacement of the acoustic transducer 322 is transferred to the sample container 12.

The chamber 20 includes a light port 28 through which photonic emissions 17 generated by the organisms propagate to an optical detector system 30 mounted in a light tight manner on the chamber 20 so that only photonic emissions 17 generated by the bioluminescent organisms. Therefore, no ambient light is allowed to saturate and damage the photodetector 342 of the optical detecting system 30 when the system 320 is operational. The optical detector system 30 detects any photonic emissions 17 generated by the test organisms 16 and comprises a housing 334 in which an optical fiber bundle 338 optionally may be mounted to propagate photonic emissions 17 from a region which may have a rectangular area, such as light port 28, to a region which may have a circular region. The housing 334 includes an optical attenuator 340 and a photodetector 342. The optical attenuator 340 may preferably be implemented as a variable optical attenuator (VOA) having transmissibility that may be modulated to limit the intensity of light irradiating the photodetector 342 within the linear response range of the photodetector. The optical attenuator 342 also prevents the photodetector 342 from being saturated, as for example, from ambient light. The photodetector 342 transforms detected light, such as photonic emissions 17, into an electrical output signal, DATA, and may be of the type described above with reference to FIG. 7. A controller 32 controls the operation of the photodetector 342 via signal line PHTDTCR CNRL, the VOA 340 via signal VOA CNTRL, and the acoustic transducer 322 via signal ACOUSTIC CNTRL. By way of example, the optical attenuator 340 may be implemented as a variable optical attenuator (VOA) by which the intensity of any light propagated through the VOA may be selectively modulated (attenuated) by a variable amplifier voltage generator, not shown included in controller 32.

A safety interlock circuit 300, described above with reference to FIGS. 4 and 9–10, is located at the top of the chamber 20 and provides an output signal OPEN to the controller 32, indicating whether the cap 325 is fitted in place on top of the chamber 20 so as to prevent ambient light from saturating and damaging the photodetector 342. The safety interlock circuit 300 provides an output signal OPEN to the controller 332 so that if ambient light enters the chamber 20, the level of VOA CNTRL generated by the controller 32 causes the VOA 340 to fully occlude or block all light from reaching the photodetector 342. When the value of OPEN indicates no ambient light is entering cavity 18 of chamber 20, VOA CNTRL causes the optical transmissibility of the VOA 340 to be at a maximum.

Figure 13:
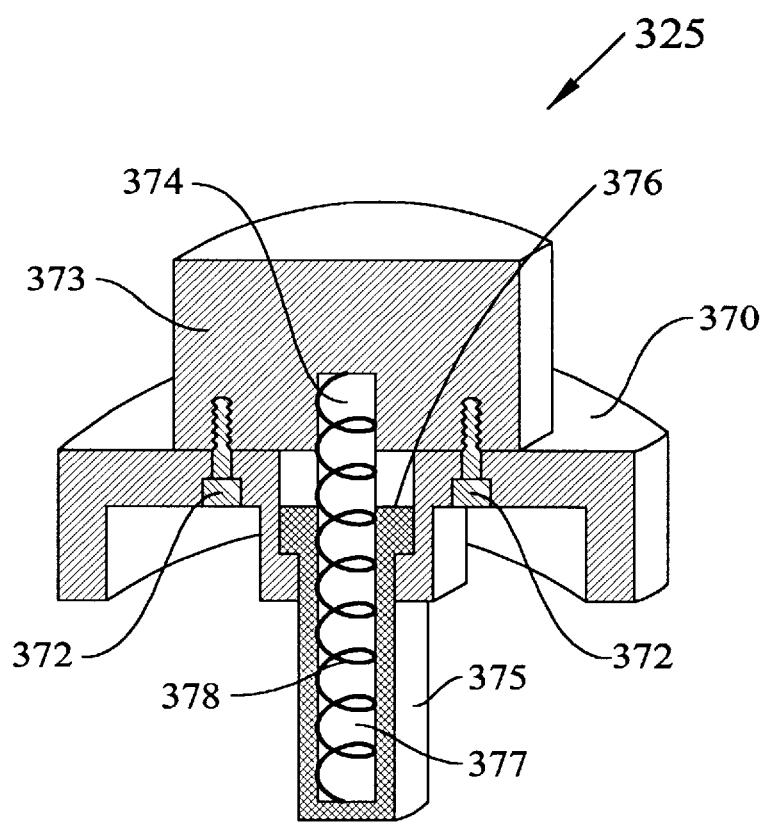
FIG. 13 is a cross-sectional perspective view of the cap.

The cap 325, described with reference to FIG. 13, includes a generally disk-shaped base 370 having a center throughbore 371 with an annular land at the bottom end of the bore, and a ring-shaped, 360-degree groove, sized to slide over the annulus 55 shown in FIG. 4 of the chamber 20 with a minimum of clearance. The cap 325 also includes a generally cylindrically-shaped retainer element 373 which may be attached to the base section 370 with two or three countersunk bolts 372. The retainer element 373 includes a bore 374 which is coaxially aligned and coterminous with the throughbore 371 when the retainer is attached to the base 370. The bore 374 does not extend completely through the retainer 373. A spring actuated element, such as a piston 375, having an annular land 376 and a bore 377 is fitted through the throughbore 376 of the base 370. A spring 378, compressed within the bores 374 and 377, forces the piston 375 downward to hold the sample container 12 against the acoustic transducer 322 when the cap 325 is fitted in place on the light tight chamber 20. The spring 378 is preferably made of stainless steel to resist corrosion. The outside diameter of the piston 375 is preferably equal to the shortest cross-sectional outside length across the sample container 12.

Referring again to FIG. 11, the system 320 also includes a start switch 33 coupled to the controller 32 which allows the optical detector system 30 and acoustic transducer 322 to be automatically enabled in an appropriate time sequence. A second switch 37 operably coupled to the controller 32 and to the optical detector system 30 provides a human operator the option of operating the system 3210 in either an automatic or manual mode, or of disabling the system altogether when the switch 37 is placed in the OFF position. The controller 32, and switches 33 and 37 may be of the type described above with reference to FIGS. 1, 9, and 10.

Figure 14:
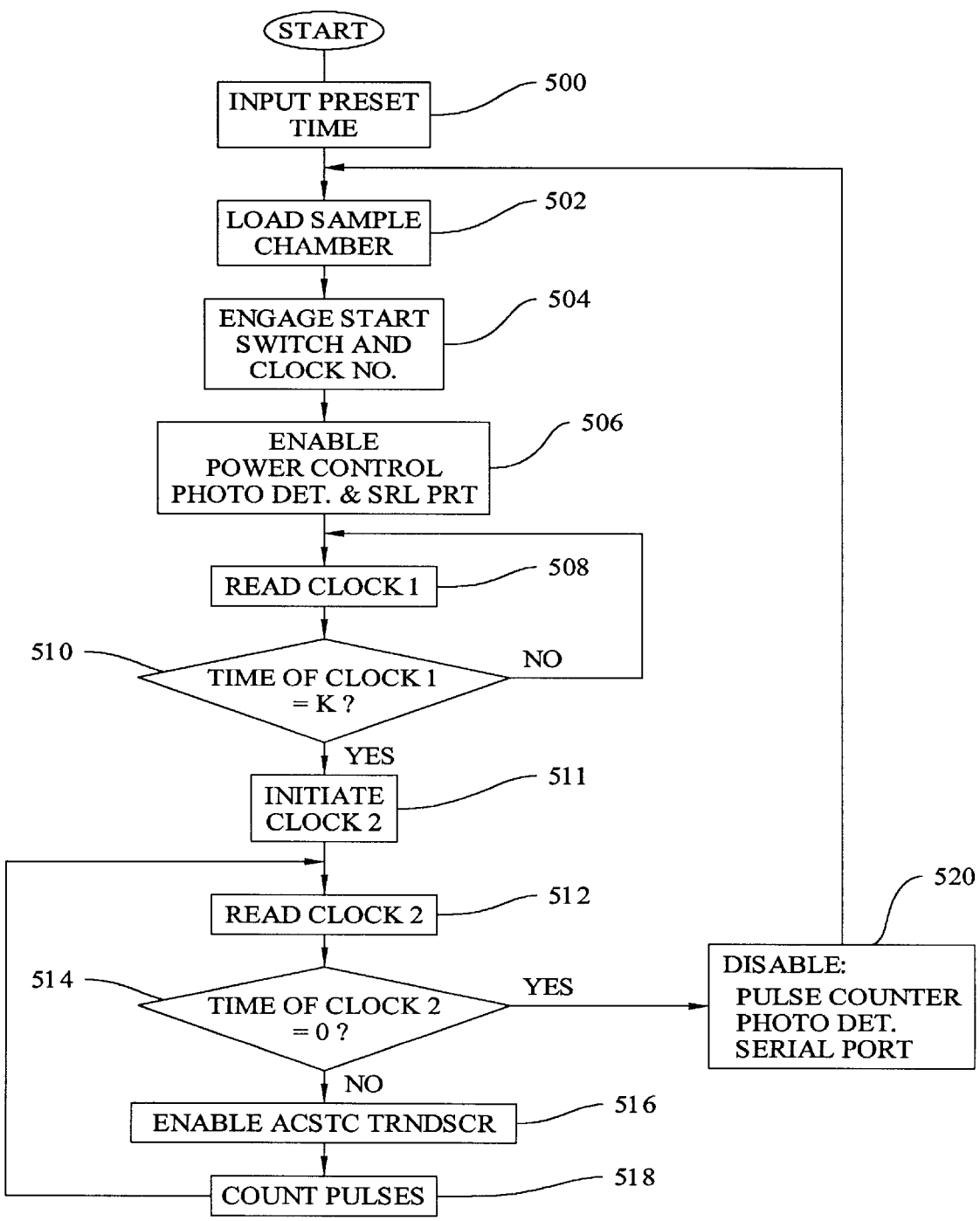
FIG. 14 is a flow chart of the bioluminescent bioassay system shown in FIG. 11.

The operation of the system 310 is described with reference to FIG. 14. The system 320 is initialized by providing an input representing the desired counting time, "TIME", to the controller 32 at step 500. The counting time refers to the period in which electronic pulses corresponding to the photonic emissions 17 generated by the bioluminescent organisms 16 are to be counted. Next, at step 502, the aqueous sample solution 14 with the bioluminescent organisms 16 may be placed in the sample container 12. The sample holder 12 is placed in the sample support 21 which is mounted within the light tight chamber 20. A human operator then fits the cap 325 to the light tight body 20 so that no ambient light enters the chamber 18, and so therefore, no ambient light falls incident on the photodetector 342. At step 504, the operation of the controller 32 is initiated by pushing the "START" switch 33 to enable the photodetector 342 and initiate a first internal clock, CLOCK 1, in the controller 32. The controller 32 enables the photodetector 342, as well as the serial port 35 at step 506.

The controller 32 then reads the first clock at step 508. A decision is made by the controller at step 510 to determine if the time elapsed from the initiation of the first clock equals a predetermined value, K. If the determination at step 510 is "NO", then the controller 32 returns to step 508. If the determination at step 510 is YES, the controller 32 initiates a second clock, CLOCK 2, at step 511 which counts down from a time, d+TIME, where "d" represents a delay, by way of example, of two seconds to assure that the organisms 16 have not been pre-stimulated. The controller 32 then reads CLOCK 2 at step 512. Proceeding to step 514, the controller 32 determines if the time indicated by the second clock equals zero. If the determination at step 514 is "NO", the controller 32 enables the acoustic transducer 322 at step 516, and then at step 518, allows the controller 32 to count pulses generated by the photodetector 342. The controller 32 then returns to step 512. If the determination by the controller at step 514 is "YES", then at step 520, the controller 32 disables the photodetector 342, acoustic transducer 322, and serial port 35, and ceases to count pulses generated by the photodetector 342. The operation of the system then returns to step 502.

While CLOCK 2 decrements, any photons emitted by the organisms 16 detected by the photodetector 342 cause the photodetector to generate an electric pulse which is counted by the controller 32. Generally, while CLOCK 2 is decrements, an output data signal, OUTPUT DATA, is sent to output port 35, such as an RS-232 serial port, of the controller 32. The signal OUTPUT DATA may, for example, include elapsed time and count data, The output data signal may also be sent to a digital display 155 integrated with the controller 32. Thus, the output data signal may be sent to a remote computer to log and analyze data, or to a peripheral device such as a printer, not shown.

Obviously, many modifications and variations of the present invention are possible in light of the above teachings. For example, the light detecting element in the light detector system 30 may be implemented as a vacuum avalanche diode or as a blue enhanced photo diode array. It is therefore to be understood that within the scope of the appended claims, the invention may be practiced otherwise than as specifically described.

We claim:

1. A system for measuring the toxicity of an aqueous solution, comprising:
    a light tight chamber having a cavity for holding a sample container containing an aqueous test solution of bioluminescent organisms;
    a vibration generating system mounted to said light tight chamber for generating pressure pulses in said test solution;
    a light detector system for detecting light emitted by said bioluminescent organisms and for generating electric pulses in response to detecting said detected light emissions; and
    a controller for controlling said vibration generating system and said light detector system, and for counting said electric pulses within a predetermined period of time.

2. The system of claim 1 further including a bar code scanner for reading bar codes on said sample container and for storing data representations of said bar codes.

3. The system of claim 1 wherein said light detector system includes a photodetector and a variable optical attenuator optically aligned with said photodetector.

4. The system of claim 3 wherein said controller modulates the optical transmissibility of said variable optical attenuator.

5. The system of claim 3 wherein said light detector system includes a fiber optic bundle for propagating said light emissions from said light tight chamber to said photodetector.

6. The system of claim 3 wherein said photodetector is a photomultiplier tube.

7. The system of claim 1 wherein said vibration generating system includes an acoustic transducer.

8. The system of claim 7 wherein said acoustic transducer is U-shaped.

9. The system of claim 7 wherein said acoustic transducer is an ultrasonic transducer.

10. The system of claim 7 wherein said acoustic transducer is a piezoelectric transducer.

11. The system of claim 3 wherein said optical detector system includes an optical filter optically aligned with said photodetector.

12. The system of claim 1 further including a sample container having a bar code for holding a test solution.

13. The system of claim 1 wherein said sample container holds a solution of bioluminescent organisms.

14. The system of claim 9 wherein said bioluminescent organisms include *Gonyalaux polyedra*.

15. The system of claim 1 further including a lift mechanism for removing said sample container from said light tight chamber.

16. The system of claim 3 further including:
    a switch operably coupled to said optical detector system; and
    an interlock circuit for disabling said light detector system when ambient light penetrates said light tight chamber to prevent said controller from enabling said photodetector until said switch is manually toggled.

17. The system of claim 7 in which said light tight chamber includes a cap having a spring actuated element for urging said sample chamber against said vibration generating system.

18. A system for measuring the toxicity of an aqueous solution, comprising:
    a light tight chamber having a cavity for holding a sample container containing an aqueous test solution of bioluminescent organisms;
    an acoustic generating system mounted to said light tight chamber for generating pressure pulses in said test solution;
    a light detector system, including a photodetector and an optical attenuator, for detecting light emissions generated by said bioluminescent organisms and for generating electric pulses in response to detecting each of said detected light emissions;
    a controller for controlling said vibration generating system and said light detector system, and for counting said electric pulses within a predetermined period of time; and
    a bar code scanner for reading bar codes on said sample container and for storing data representations of said bar codes.

19. The system of claim 18 wherein said optical attenuator is a variable optical attenuator which prevents saturation of said photodetector.

20. The system of claim 19 wherein said controller modulates the optical transmissibility of said variable optical attenuator.

21. The system of claim 19 wherein said light detector system includes a fiber optic bundle for propagating said light emissions from said light tight chamber to said photodetector.

22. The system of claim 18 wherein said photodetector is a photomultiplier tube.

23. The system of claim 18 wherein said acoustic transducer is U-shaped.

24. The system of claim 18 wherein said acoustic transducer is an ultrasonic transducer.

25. The system of claim 18 wherein said acoustic transducer is a piezoelectric transducer.

26. The system of claim 18 wherein said optical detector system includes an optical filter optically aligned with said photodetector.

27. The system of claim 18 further including a sample container having a bar code for holding a test solution.

28. The system of claim 18 wherein said sample container holds a solution of bioluminescent organisms.

29. The system of claim 18 wherein said bioluminescent organisms include *Gonyalaux polyedra*.

30. The system of claim 18 further including a lift mechanism for removing said sample container from said light tight chamber.

31. The system of claim 18 further including:
    a switch operably coupled to said optical detector system; and
    an interlock circuit for disabling said light detector system when ambient light penetrates said light tight chamber to prevent said controller from enabling said photodetector until said switch is manually toggled.

32. The system of claim 18 wherein said bar code scanning system includes a bar code scanner for reading said bar codes and a data processor for storing data representations of said bar codes.

33. The system of claim 18 in which said light tight chamber includes a cap having a spring actuated element for urging said sample chamber against said vibration generating system.

* * * * *